United States Patent [19]

Almansa et al.

[11] Patent Number: 5,356,915
[45] Date of Patent: Oct. 18, 1994

[54] TETRALONES WITH PHARMACOLOGICAL ACTIVITY, COMPOSITIONS CONTAINING THEM

[75] Inventors: Carmen Almansa; Concepción González; Ma. Carmen Torres; Elena Carceller; Javier Bartrolí, all of Barcelona, Spain

[73] Assignee: J. Uriach & Cia. S.A., Barcelona, Spain

[21] Appl. No.: 49,865

[22] Filed: Apr. 20, 1993

[30] Foreign Application Priority Data

Oct. 19, 1992 [ES] Spain .................... 92 02203

[51] Int. Cl.$^5$ .................... A61K 31/44; C07D 213/89
[52] U.S. Cl. .................... 514/357; 514/336; 514/277; 546/330; 546/268; 546/340
[58] Field of Search .................... 546/268, 330, 340; 514/336, 357, 277

[56] References Cited

U.S. PATENT DOCUMENTS 5,132,307 7/1992 Baumgarth et al. .................... 514/247
5,208,246 5/1993 Almansa et al. .................... 546/301

FOREIGN PATENT DOCUMENTS 168619 1/1986 European Pat. Off. .
298452 1/1989 European Pat. Off. .
368160 5/1990 European Pat. Off. .
489300 6/1992 European Pat. Off. .
525768 2/1993 European Pat. Off. .
2318625 2/1977 France .

OTHER PUBLICATIONS

R. W. Griffin, J. D. Gass, M. A. Berwick, R. S. Shulman, J. Org. Chem., 1964, 29, 2109.
Chemical Abstracts, vol. 85, No. 19, 8 Nov. 1976, abstract No. 142883u, V. P. Barve et al., Indian J. Chem., Sect. B., vol. 14B, No. 2 (1976), pp. 84–87.
Chemical Abstracts, vol. 65, No. 1, 4 Jul. 1966, abstract No. 665d, G. Traverso et al., Farmaco Ed. Sci., vol. 21, No. 1 (1966), pp. 35–50.
European Search Report dated Feb. 2, 1994 for corresponding European patent application No. 93107289.6.

Primary Examiner—Jane T. Fan
Attorney, Agent, or Firm—Rothwell, Figg, Ernst & Kurz

[57] ABSTRACT

The present invention relates to new tetralones having formula I:

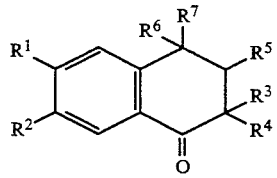

wherein $R^1$ to $R^7$ are as defined in claim 1. The invention also relates to processes for their preparation, to pharmaceutical compositions containing them and to their use in the manufacture of medicaments. These compounds are antihypertensive and bronchodilator agents.

24 Claims, No Drawings

TETRALONES WITH PHARMACOLOGICAL ACTIVITY, COMPOSITIONS CONTAINING THEM

BACKGROUND OF THE INVENTION

1. Field of the invention.

The present invention relates to novel tetralones with pharmacological activity. The invention also relates to a process for their preparation, to pharmaceutical compositions containing them and to their use for the manufacture of medicaments useful in the treatment of mammals, including man. Such tetralones have been found to have blood pressure lowering activity, useful in the treatment of hypertension, as well as bronchodilatory activity, useful in the treatment of asthma. They are also indicated in the treatment of other diseases related with the regulation of the smooth muscle contraction in the gastrointestinal, uterus or urinary tract and in the cardiovascular, respiratory or cerebrovascular systems. Such disorders include angina, congestive heart failure, incontinence, irritable bowel syndrome and epilepsy.

2. Description of the Prior Art.

Several tetralones having antihypertensive activity have been described in the literature, all of them different from the compounds of the present invention.

Our patent applications EP 489300 and EP 525768 disclose certain tetralones with antihypertensive activity of general formula:

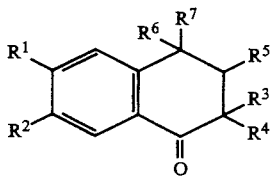

wherein $R^1$ and $R^2$ represent, among others, hydrogen, cyano, nitro, halogen, trifluoromethyl, pentafluoroethyl, hydroxy, $C_{1-4}$ alkyl, $C_{1-4}$ alkoxy, amino, amino substituted by one or two $C_{1-4}$ alkyl groups; $R^3$ is hydrogen or $C_{1-4}$ alkyl; $R^4$ is $C_{1-4}$ alkyl, or $R^3$ and $R^4$ together form a $C_{2-5}$ polymethylene chain; $R^5$ is hydroxy or acetoxy and $R^6$ is hydrogen, or $R^5$-$R^6$ together form a bond; and $R^7$ represents a cyclic amide or thioamide, saturated or insaturated and optionally substituted, which is bonded to the tetralone ring through the nitrogen atom of the amide moiety, or else $R^7$ represents a radical —$OR^8$, wherein $R^8$ represents certain optionally substituted heterocycles, or $R^7$ represents an open-chained amine or amide carrying different aliphatic, aromatic or heterocyclic substituents.

The present invention describes new compounds structurally related to the ones described therein, where the nature of the substituent in position 4 of the tetralone ring has been substantially modified.

DESCRIPTION OF THE INVENTION

The present invention relates to new tetralones of general formula I:

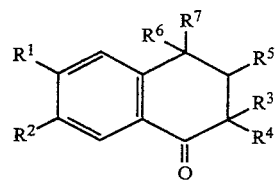

wherein:

$R^1$ and $R^2$ independently represent hydrogen, $C_{1-4}$ alkyl, hydroxy, $C_{1-4}$ alkoxy, formyl, $C_{1-4}$ alkylcarbonyl, $C_{1-4}$ alkylthiocarbonyl, carboxyl, $C_{1-4}$ alkoxycarbonyl, $C_{1-4}$ alkoxythiocarbonyl, $C_{1-4}$ alkylcarbonyloxy, $C_{1-4}$ alkylthiocarbonyloxy, hydroxy-($C_{1-4}$) alkyl, mercapto-($C_{1-4}$)alkyl, perfluoro($C_{1-4}$)alkyl, nitro, amino, cyano, halogen, trifluoromethoxy, ethynyl, trimethylsilylethynyl, $C_{1-4}$ alkylsulfinyl, arylsulfinyl, $C_{1-4}$ alkylsulfonyl, arylsulfonyl, $C_{1-4}$ alkoxysulfinyl, $C_{1-4}$ alkoxysulfonyl, $C_{1-4}$ alkylcarbonylamino, $C_{1-4}$ alkoxycarbonylamino, aminosulfinyl, aminosulfonyl, aminocarbonyl, aminothiocarbonyl, $C_{1-4}$ alkylsulfinylamino, $C_{1-4}$ alkylsulfonylamino, $C_{1-4}$ alkoxysulfinylamino, $C_{1-4}$ alkoxysulfonylamino, ($C_{1-4}$ alkyl)carbonyl($C_{1-4}$ alkyl), nitro-($C_{1-4}$ alkyl), cyano-($C_{1-4}$ alkyl), ($C_{1-4}$ alkyl)C(=NOH), ($C_{1-4}$ alkyl)C(=NNH$_2$) or ($C_{1-4}$ alkoxy)C(=NH), the above amino groups being optionally substituted by one or two $C_{1-4}$ alkyl groups;

$R^3$ and $R^4$ are the same or different and independently represent a $C_{1-4}$ alkyl group, or $R^3$ and $R^4$ together form a $C_{2-5}$ polymethylene chain;

$R^5$ is hydrogen and then $R^6$ represents hydrogen, hydroxy or $C_{1-4}$ alkoxy, or $R^5$ is hydroxy and then $R^6$ is hydrogen, or else $R^5$ and $R^6$ together with the ring carbons form a bond or a group of formula:

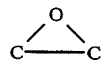

$R^7$ is a 2-, 3- or 4-pyridyl radical which can be optionally substituted by a hydroxy group or whose nitrogen atom can be optionally in the form of the N-oxide; and the salts and solvates thereof.

The invention also provides the use of at least one compound of formula I or a pharmaceutically acceptable salt thereof or a pharmaceutically acceptable solvate thereof in treatment and/or prevention of the diseases related with the regulation of the smooth muscle contraction at the cardiovascular, respiratory and cerebrovascular systems, and at the gastrointestinal, urinary and uterus tracts, and particularly for the treatment and/or prevention of hypertension and asthma in mammals, including man.

The invention further provides a pharmaceutical composition which comprises an effective amount of at least one compound of formula I or a pharmaceutically acceptable salt thereof or a pharmaceutically acceptable solvate thereof in admixture with a pharmaceutically acceptable excipient.

The invention still further provides a process for preparing the compounds of formula I, which in general terms comprises:

(a) reacting a compound of general formula II, wherein $R^1$ and $R^2$ are as defined above,

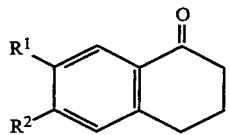

with a compound of general formula $R^{7'}$—X (III, wherein $R^{7'}$ is a 2-, 3- or 4-pyridyl radical which can be optionally substituted by a hydroxy group and X means chlorine, bromine or iodine) in the presence of a base such as butyl lithium in a polar solvent such as diethyl ether, to give a compound of general formula IV:

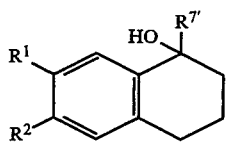

wherein $R^1$, $R^2$ and $R^{7'}$ have the previously defined meaning, which is then allowed to react with an oxidant such as potassium permanganate in a suitable solvent such as acetone, to give a compound of general formula V:

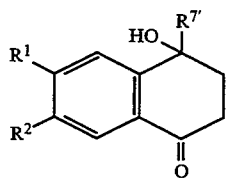

wherein $R^1$, $R^2$ and $R^{7'}$ have the previously defined meaning, and subsequently protecting the hydroxy group in a compound of formula V to give a compound of formula VI

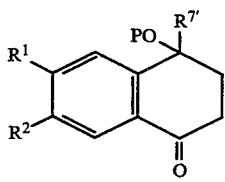

wherein $R^1$, $R^2$ and $R^{7'}$ have the previously defined meaning and P is a hydroxy protecting group, which is then allowed to react with a base such as sodium hydride or butyl lithium and an alkylating agent of general formula $R^3$—X (VII, wherein $R^3$ and X have the previously defined meaning) in an inert solvent such as benzene or tetrahydrofuran, and subsequently treating the compound thus obtained with more base and an alkylating agent of general formula R4-X (VIII, wherein $R^4$ and X have the previously defined meaning), to give a compound of formula IX

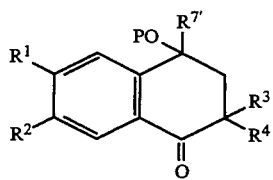

wherein $R^1$, $R^2$, $R^3$, $R^4$, $R^{7'}$ and P have the previously defined meaning, or alternatively, in case $R^3$ and $R^4$ are the same, dialkylation of VI can be performed directly by using two equivalents of base and an excess of alkylating agent or else V can be directly dialkylated by using 3 equivalents of base and two equivalents of alkylating agent in the same experimental conditions mentioned above, and finally deprotecting the hydroxy group of a compound of formula IX, which optionally can be then alkylated by treatment with a base such as sodium hydride or butyl lithium and an alkylating agent of formula A—X, wherein A means $C_{1-4}$ alkyl and X has the previously defined meaning, in the same experimental conditions mentioned above; or alternatively, in case $R^3$, $R^4$ and A are the same, polyalkylation can be performed directly by treatment of V with three equivalents of base and an excess of alkylating agent; or when in a compound of formula I, $R^6$ is $C_{1-4}$ alkoxy, I may also be obtained by reacting a compound of formula IV with an alkylating agent of formula A-X in the same experimental conditions mentioned above, to give a compound of formula X

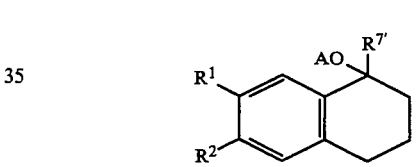

wherein $R^1$, $R^2$, $R^{7'}$ and A have the previously defined meaning, which is then allowed to react with an oxidant such as potassium permanganate in the same experimental conditions mentioned above to give a compound of formula XI

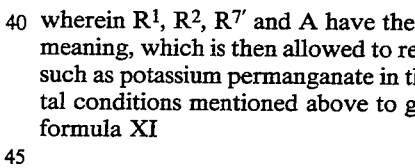

wherein $R^1$, $R^2$, $R^{7'}$ and A have the previously defined meaning, which is then alkylated in the same experimental conditions mentioned above for the alkylation of VI;

(b) in all cases wherein $R^5$ and $R^6$ together with the ring carbons form a double bond, reacting a compound of general formula I wherein R5 is hydrogen and $R^6$ is hydroxy or $C^{1-4}$ alkoxy with p-toluenesulfonic acid in a suitable solvent such as toluene or xylene, removing the water formed by azeotropic distillation, and optionally, reducing the double bond with hydrogen in the presence of a catalyst such as palladium on charcoal in a polar solvent such as ethanol;

(c) in all cases wherein $R^7$ is a 2-, 3- or 4-pyridyl group whose nitrogen atom is in form of the N-oxide, reacting a compound of formula I wherein $R^7$ is a 2-, 3- or 4-pyridyl group with a peracid such as m-chloroperbenzoic acid in a suitable solvent such as methylene chloride; and optionally, in case $R^5$ and $R^6$ together with the ring carbons form a double bond, said bond can be simultaneously epoxidated by treatment with an excess of peracid, and optionally, the epoxide thus obtained can be hydrogenated with hydrogen in the presence of a catalyst such as palladium on charcoal in a polar solvent such as ethanol;

(d) optionally, interconverting the groups $R^1$ and/or $R^2$ in a compound of formula I or any synthetic intermediate into other groups $R^1$ and/or $R^2$;

(e) and optionally, reacting a compound of formula I with an acid to give its corresponding acid addition salt.

In the compounds of the present invention, a $C_{1-4}$ alkyl group means a linear or branched alkyl chain containing from 1 to 4 carbon atoms and includes methyl, ethyl, propyl, isopropyl, butyl, isobutyl, sec-butyl or tert-butyl, of which methyl, ethyl, propyl, isopropyl, butyl and isobutyl are preferred, methyl and ethyl are more preferred, and methyl is most preferred.

A "$C_{1-4}$ alkoxy" group means a group derived from the union of a $C_{1-4}$ alkyl group to an oxygen atom of an ether functional group. Examples include methoxy, ethoxy, propoxy, isopropoxy, butoxy, isobutoxy, sec-butoxy and tert butoxy, of which methoxy, ethoxy, propoxy, isopropoxy, butoxy and isobutoxy are preferred, and methoxy is most preferred.

In $R^1$ or $R^2$ a $C_{1-4}$ alkylcarbonyl group means a group derived from the union of a $C_{1-4}$ alkyl group to a carbonyl group. Examples include acetyl, propanoyl, isopropanoyl, butanoyl, and isobutanoyl, of which acetyl and propanoyl are preferred, and acetyl is most preferred.

In $R^1$ or $R^2$ a $C_{1-4}$ alkylthiocarbonyl group means a group derived from the union of a $C_{1-4}$ alkyl group to a thiocarbonyl group. Examples include thioacetyl, thiopropanoyl, thioisopropanoyl, thiobutanoyl, and thioisobutanoyl, of which thioacetyl and thiopropanoyl are preferred, and thioacetyl is most preferred.

In $R^1$ or $R^2$ a $C_{1-4}$ alkoxycarbonyl group means a group derived from the union of a $C_{1-4}$ alkoxy group, like the above mentioned, to a carbonyl group, and include methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, of which methoxycarbonyl, ethoxycarbonyl, propoxycarbonyl, isopropoxycarbonyl, butoxycarbonyl, and isobutoxycarbonyl are preferred, methoxycarbonyl and ethoxycarbonyl are more preferred, and methoxycarbonyl is most preferred.

In $R^1$ or $R^2$ a $C_{1-4}$ alkoxythiocarbonyl group means a group derived from the union of a $C_{1-4}$ alkoxy group, like the above mentioned, to a thiocarbonyl group, and include methoxythiocarbonyl, ethoxythiocarbonyl, propoxythiocarbonyl, isopropoxythiocarbonyl, butoxythiocarbonyl, isobutoxythiocarbonyl, sec-butoxythiocarbonyl and tert-butoxythiocarbonyl, of which methoxythiocarbonyl, ethoxythiocarbonyl, propoxythiocarbonyl, isopropoxythiocarbonyl, butoxythiocarbonyl, and isobutoxythiocarbonyl are preferred, methoxythiocarbonyl and ethoxythiocarbonyl are more preferred, and methoxythiocarbonyl is most preferred.

In $R^1$ or $R^2$ a $C_{1-4}$ alkylcarbonyloxy group means a group derived from the union of a $C_{1-4}$ alkylcarbonyl group to an oxygen atom. Examples include acetoxy, propanoxy, isopropanoxy, butanoxy, and isobutanoxy, of which acetoxy and propanoxy are preferred, and acetoxy is most preferred.

In $R^1$ or $R^2$ a $C_{1-4}$ alkylthiocarbonyloxy group means a group derived from the union of a $C_{1-4}$ alkylthiocarbonyl group to an oxygen atom. Examples include thioacetoxy, thiopropanoxy, thioisopropanoxy, thiobutanoxy, and thioisobutanoxy, of which thioacetoxy and thiopropanoxy are preferred, and thioacetoxy is most preferred.

In $R^1$ or $R^2$ a hydroxy-$C_{1-4}$ alkyl group means a group resulting from the substitution of one hydrogen atom of the above mentioned "$C_{1-4}$ alkyl" group by an hydroxyl group. Examples include hydroxymethyl, 1-hydroxyethyl, 2-hydroxyethyl, 1-hydroxypropyl, 2-hydroxypropyl, and 3-hydroxypropyl, of which hydroxymethyl, 1-hydroxyethyl and 2-hydroxyethyl are preferred.

In $R^1$ or $R^2$ a mercapto-$C_{1-4}$ alkyl group means a group resulting from the substitution of one hydrogen atom of the above mentioned "$C_{1-4}$ alkyl" group by a mercapto group. Examples include mercaptomethyl, 1-mercaptoethyl, 2-mercaptoethyl, 1-mercaptopropyl, 2-mercaptopropyl, and 3-mercaptopropyl, of which mercaptomethyl, 1-mercaptoethyl and 2-mercaptoethyl are preferred.

In $R^1$ or $R^2$ a perfluoro($C_{1-4}$)alkyl group means a $C_{1-4}$ alkyl group in which all hydrogen atoms have been substituted by fluorine atoms. Examples include trifluoromethyl, pentafluoroethyl, heptafluoropropyl, and nonafluorobutyl, of which trifluoromethyl and pentafluoroethyl are preferred.

In a compound of formula I, an amino group may be optionally substituted by one or two $C_{1-4}$ alkyl groups. An amino group substituted by one or two $C_{1-4}$ alkyl groups means a group resulting from the substitution of one or two hydrogen atoms of the amino group by a $C_{1-4}$ alkyl group. When the amino group is substituted by two $C_{1-4}$ alkyl groups, they can be the same or different. Examples include amino, methylamino, dimethylamino, ethylamino, diethylamino, ethylmethylamino, propylamino, dipropylamino, isopropylamino, and diisopropylamino, of which methylamino, dimethylamino, ethylamino and diethylamino are preferred, and methylamino and dimethylamino are most preferred.

The term "halogen" means fluorine, chlorine, bromine or iodine.

In $R^1$ or $R^2$ a $C_{1-4}$ alkylsulfinyl group means a group derived from the union of a $C_{1-4}$ alkyl group to a sulfinyl group. Examples include methylsulfinyl, ethylsulfinyl, propylsulfinyl, isopropylsulfinyl, butylsulfinyl, isobutylsulfinyl, sec-butylsulfinyl and tert-butylsulfinyl, of which methylsulfinyl, ethylsulfinyl, propylsulfinyl, isopropylsulfinyl, butylsulfinyl and isobutylsulfinyl are preferred, and methylsulfinyl is most preferred.

In a compound of formula I, the term "aryl" represents a phenyl group or a phenyl group substituted by a fluorine, chlorine, bromine or iodine atom, or a methyl, hydroxyl, methoxy, cyano or nitro group. Examples include phenyl, 2-methylphenyl, 4-methylphenyl, 4-chlorophenyl, 4-bromophenyl, 4-methoxyphenyl, 2-methoxyphenyl, and 4-cyanophenyl.

In $R^1$ or $R^2$ an arylsulfinyl group means a group derived from the union of an aryl group, like the above mentioned, to a sulfinyl group. Examples include phenylsulfinyl, 2-methylphenylsulfinyl, 4-methylphenylsulfinyl, 4-chlorophenylsulfinyl, 4-bromophenylsulfinyl, 4-methoxyphenylsulfinyl, 2-methoxyphenylsulfinyl, and 4-cyanophenylsulfinyl, of which phenylsulfinyl is preferred.

In $R^1$ or $R^2$ a $C_{1-4}$ alkylsulfonyl group means a group derived from the union of a $C_{1-4}$ alkyl group to a sulfonyl group. Examples include methylsulfonyl, ethylsulfonyl, propylsulfonyl, isopropylsulfonyl, butylsulfonyl, isobutylsulfonyl, sec-butylsulfonyl and tert-butylsulfonyl, of which methylsulfonyl, ethylsulfonyl, propylsulfonyl, isopropylsulfonyl, butylsulfonyl and isobutylsulfonyl are preferred, and methylsulfonyl is most preferred.

In $R^1$ or $R^2$ an arylsulfonyl group means a group derived from the union of an aryl group, like the above mentioned, to a sulfonyl group. Examples include phenylsulfonyl, 2-methylphenylsulfonyl, 4-methylphenylsulfonyl, 4-chlorophenylsulfonyl, 4-bromophenylsulfonyl, 4-methoxyphenylsulfonyl, 2-methoxyphenylsulfonyl, and 4-cyanophenylsulfonyl, of which phenylsulfonyl is preferred.

In $R^1$ or $R^2$ a $C_{1-4}$ alkoxysulfinyl group means a group derived from the union of a $C_{1-4}$ alkoxy group to a sulfinyl group. Examples include methoxysulfinyl, ethoxysulfinyl, propoxysulfinyl, isopropoxysulfinyl, butoxysulfinyl, isobutoxysulfinyl, sec-butoxysulfinyl and tert-butoxysulfinyl, of which methoxysulfinyl, ethoxysulfinyl, propoxysulfinyl, isopropoxysulfinyl, butoxysulfinyl and isobutoxysulfinyl are preferred, and methoxysulfinyl is most preferred.

In $R^1$ or $R^2$ a $C_{1-4}$ alkoxysulfonyl group means a group derived from the union of a C1-4 alkoxy group to a sulfonyl group. Examples include methoxysulfonyl, ethoxysulfonyl, propoxysulfonyl, isopropoxysulfonyl, butoxysulfonyl, isobutoxysulfonyl, sec-butoxysulfonyl and tert-butoxysulfonyl, of which methoxysulfonyl, ethoxysulfonyl, propoxysulfonyl, isopropoxysulfonyl, butoxysulfonyl and isobutoxysulfonyl are preferred, and methoxysulfonyl is most preferred.

In $R^1$ or $R^2$ a $C_{1-4}$ alkylcarbonylamino group means a group derived from the substitution of an hydrogen atom of an amino group, like the above mentioned, by a $C_{1-4}$ alkylcarbonyl group. Examples include acetamido, N-methylacetamido, propanamido, N-methylpropanamido, and isopropanamido, of which acetamido, N-methylacetamido, propanamido and N-methylpropanamido are preferred, and acetamido and N-methylacetamido are most preferred.

In $R^1$ or $R2$ a $C_{1-4}$ alkoxycarbonylamino group means a group derived from the substitution of an hydrogen atom of an amino group, like the above mentioned, by a $C_{1-4}$ alkoxycarbonyl group. Examples include methoxycarbonylamino, ethoxycarbonylamino, propoxycarbonylamino, isopropoxycarbonylamino, butoxycarbonylamino, and isobutoxycarbonylamino, of which methoxycarbonylamino and ethoxycarbonylamino are preferred, and methoxycarbonylamino is most preferred.

In $R^1$ or $R^2$ an aminosulfinyl group means a group derived from the union of an amino group, like the above mentioned, to a sulfinyl group, and includes, among others, aminosulfinyl, methylaminosulfinyl, dimethylaminosulfinyl, ethylaminosulfinyl, diethylaminosulfinyl, ethylmethylaminosulfinyl, propylaminosulfinyl, dipropylaminosulfinyl, isopropylaminosulfinyl, and diisopropylaminosulfinyl, of which aminosulfinyl, methylaminosulfinyl, dimethylaminosulfinyl, ethylaminosulfinyl, and diethylaminosulfinyl are preferred, and aminosulfinyl, methylaminosulfinyl and dimethylaminosulfinyl are most preferred.

In $R^1$ or $R^2$ an aminosulfonyl group means a group derived from the union of an amino group, like the above mentioned, to a sulfonyl group, and includes, among others, aminosulfonyl, methylaminosulfonyl, dimethylaminosulfonyl, ethylaminosulfonyl, diethylaminosulfonyl, ethylmethylaminosulfonyl, propylaminosulfonyl, dipropylaminosulfonyl, isopropylaminosulfonyl, and diisopropylaminosulfonyl, of which aminosulfonyl, methylaminosulfonyl, dimethylaminosulfonyl, ethylaminosulfonyl, and diethylaminosulfonyl are preferred, and aminosulfonyl, methylaminosulfonyl and dimethylaminosulfonyl are most preferred.

In $R^1$ or $R^2$ an aminocarbonyl group means a group derived from the union of an amino group, like the above mentioned, to a carbonyl group. Examples include aminocarbonyl, methylaminocarbonyl, dimethylaminocarbonyl, ethylaminocarbonyl, diethylaminocarbonyl, ethylmethylaminocarbonyl, propylaminocarbonyl, dipropylaminocarbonyl, isopropylaminocarbonyl, and diisopropylaminocarbonyl, of which aminocarbonyl, methylaminocarbonyl, dimethylaminocarbonyl, ethylaminocarbonyl and diethylaminocarbonyl are preferred, and aminocarbonyl, methylaminocarbonyl and dimethylaminocarbonyl are most preferred.

In $R^1$ or $R^2$ an aminothiocarbonyl group means a group derived from the union of an amino group, like the above mentioned, to a thiocarbonyl group. Examples include aminothiocarbonyl, methylaminothiocarbonyl, dimethylaminothiocarbonyl, ethylaminothiocarbonyl, diethylaminothiocarbonyl, ethylmethylaminothiocarbonyl, propylaminothiocarbonyl, dipropylaminothiocarbonyl, isopropylaminothiocarbonyl, and diisopropylaminothiocarbonyl, of which aminothiocarbonyl, methylaminothiocarbonyl, dimethylaminothiocarbonyl, ethylaminothiocarbonyl and diethylaminothiocarbonyl are preferred, and aminothiocarbonyl, methylaminothiocarbonyl and dimethylaminothiocarbonyl are most preferred.

In $R^1$ or $R^2$ a $C_{1-4}$ alkylsulfinylamino group means a group resulting from the substitution of an hydrogen atom of an amino group, like the above mentioned, by a $C_{1-4}$ alkylsulfinyl group. Examples include methylsulfinylamino, ethylsulfinylamino, propylsulfinylamino, isopropylsulfinylamino, butylsulfinylamino, isobutylsulfinylamino, sec-butylsulfinylamino and tert-butylsulfinylamino, of which methylsulfinylamino and ethylsulfinylamino are preferred, and methylsulfinylamino is most preferred.

In $R^1$ or $R^2$ a $C_{1-4}$ alkylsulfonylamino group means a group resulting from the substitution of an hydrogen atom of an amino group, like the above mentioned, by a $C_{1-4}$ alkylsulfonyl group. Examples include methylsulfonylamino, ethylsulfonylamino, propylsulfonylamino, isopropylsulfonylamino, butylsulfonylamino, isobutylsulfonylamino, sec-butylsulfonylamino and tert-butylsulfonylamino, of which methylsulfonylamino and ethylsulfonylamino are preferred, and methylsulfonylamino is most preferred.

In $R^1$ or $R^2$ a $C_{1-4}$ alkoxysulfinylamino group means a group resulting from the substitution of an hydrogen atom of an amino group, like the above mentioned, by a $C_{1-4}$ alkoxysulfinyl group. Examples include methoxysulfinylamino, ethoxysulfinylamino, propoxysulfinylamino, isopropoxysulfinylamino, butoxysulfinylamino, isobutoxysulfinylamino, sec-butoxysulfinylamino and tert-butoxysulfinylamino, of which methoxysulfinylamino and ethoxysulfinylamino are preferred, and methoxysulfinylamino is most preferred.

In $R^1$ or $R^2$ a $C_{1-4}$ alkoxysulfonylamino group means a group resulting from the substitution of an hydrogen atom of an amino group, like the above mentioned, by a $C_{1-4}$ alkoxysulfonyl group. Examples include methoxysulfonylamino, ethoxysulfonylamino, propoxysulfonylamino, isopropoxysulfonylamino, butoxysulfonylamino, isobutoxysulfonylamino, sec-butoxysulfonylamino and tert-butoxysulfonylamino, of which methoxysulfonylamino and ethoxysulfonylamino are preferred, and methoxysulfonylamino is most preferred.

In $R^1$ or $R^2$ a $(C_{1-4}$ alkyl)carbonyl$(C_{1-4}$ alkyl) group means a group derived from the union of a $(C_{1-4}$ alkyl)carbonyl group, like the above mentioned, to a $C_{1-4}$ alkyl group. Preferred examples are 2-oxopropyl, 2-oxobutyl, 3-oxobutyl and 3-oxopentyl.

In $R^1$ or $R^2$ a nitro-$(C_{1-4}$ alkyl) group means a group resulting from the substitution of an hydrogen atom of a $C_{1-4}$ alkyl group by a nitro group. Examples include nitromethyl, 1-nitroethyl, 2-nitroethyl, 1-nitropropyl, 2-nitropropyl, and 3-nitropropyl, of which nitromethyl, 1-nitroethyl and 2nitroethyl are preferred.

In $R^1$ or $R^2$ a cyano-$(C_{1-4}$ alkyl) group means a group resulting from the substitution of an hydrogen atom of a C1-4 alkyl group by a cyano group. Examples include cyanomethyl, 1-cyanoethyl, 2-cyanoethyl, 1-cyanopropyl, 2-cyanopropyl, and 3-cyanopropyl, of which cyanomethyl, 1-cyanoethyl and 2cyanoethyl are preferred.

Examples of $(C_{1-4}$ alkyl)C($=$NOH) include 1-oximinoethyl, 1-oximinopropyl, 1-oximinobutyl, 2-methyl-1-oximinopropyl, and 1-oximinopentyl, of which 1-oximinoethyl and 1-oximinopropyl are preferred, and 1-oximinoethyl is most preferred.

Examples of $(C_{1-4}$ alkyl)C($=$NNH$_2$) include 1-hidrazonoethyl, 1-hidrazonopropyl, 1-hidrazonobutyl, 2-methyl-1-hidrazonopropyl, and 1-hidrazonopentyl, of which 1-hidrazonoethyl and 1-hidrazonopropyl are preferred, and 1-hidrazonoethyl is most preferred.

Examples of $(C_{1-4}$ alkoxy)C($=$NH) include methyl imidate, ethyl imidate, propyl imidate, isopropyl imidate, and butyl imidate, of which methyl imidate and ethyl imidate are preferred, and methyl imidate is most preferred.

In a compound of formula I, $R^3$ and $R^4$ are preferred to be both $C_{1-4}$ alkyl, more preferably methyl or ethyl, and most preferably methyl.

In a compound of formula I, $R^7$ is preferred to be 2-, 3- or 4-(N-oxide)pyridyl, and more preferably 2-(N-oxide)pyridyl.

Preferred embodiments of the present invention are those compounds of formula I wherein $R^1$, $R^2$, $R^5$, $R^6$ and $R^7$ have the previously defined meaning; and $R^3$ and $R^4$ are methyl.

More preferred embodiments of the present invention are those compounds of formula I wherein $R^5$, $R^6$ and $R^7$ have the previously defined meaning;

$R^3$ and $R^4$ are methyl;

$R^1$ represents halogen, cyano, $C_{1-4}$ alkyl, $C_{1-4}$ alkylsulfonyl, arylsulfonyl, perfluoro$(C_{1-4})$alkyl or ethynyl; and $R^2$ represents hydrogen or $R^1$.

Most preferred embodiments of the present invention are those compounds of formula I wherein $R^5$ and $R^6$ have the previously defined meaning;

$R^3$ and $R^4$ are methyl;

$R^1$ represents halogen, cyano, $C_{1-4}$ alkyl, $C_{1-4}$ alkylsulfonyl, arylsulfonyl, perfluoro$(C_{1-4})$alkyl or ethynyl;

$R^2$ represents hydrogen or $R^1$; and $R^7$ represents a 2-(N-oxide)pyridyl group.

The formulae of some specific examples are represented below, together with the number corresponding to the example in which their preparation is described:

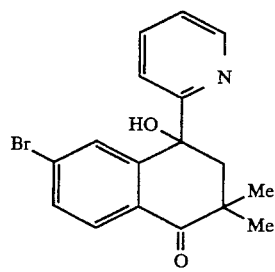

1

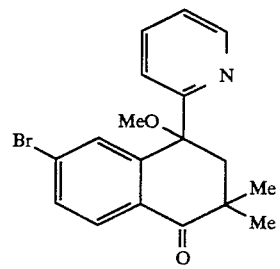

2

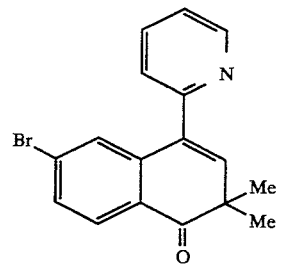

3

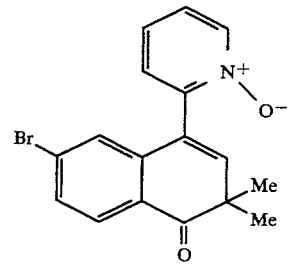

4

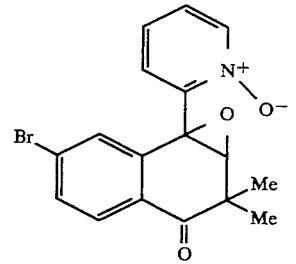

5

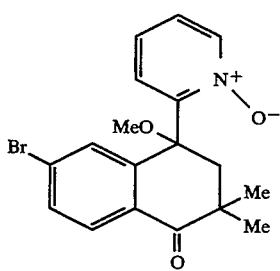
6
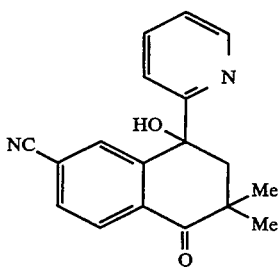
7
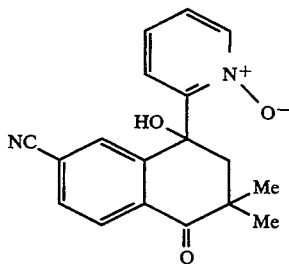
8
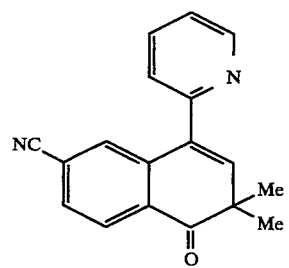
9
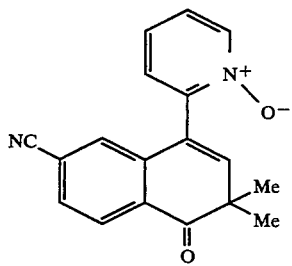
10
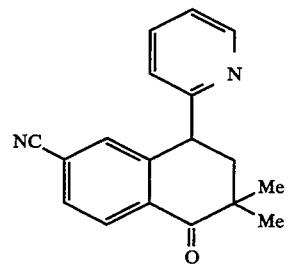
11
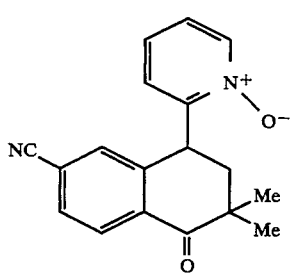
12
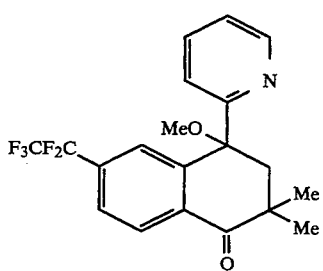
13
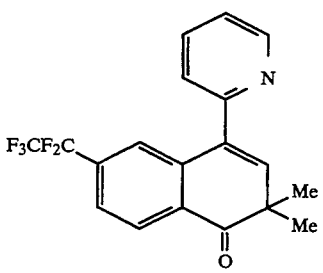
14
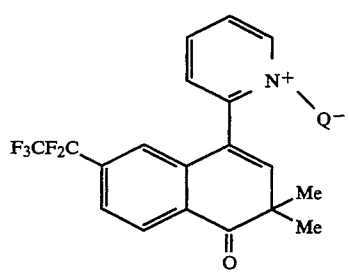
15
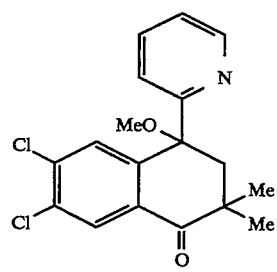
16
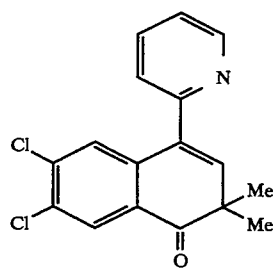
17

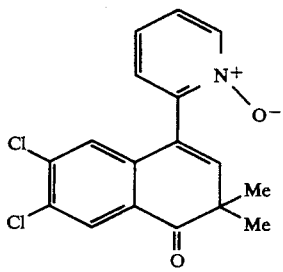

Some of the compounds of the present invention contain one or more basic nitrogen atoms and, consequently, they can form salts, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity) compared with the free compounds of formula I. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid or maleic acid.

The compounds of the present invention can exist as different diastereoisomers and/or optical isomers because the carbons in positions 3 and/or 4 of the tetralone moiety, provided that there is not a double bond between them, are chiral. Diastereoisomers can be separated by conventional techniques such as chromatography or fractional crystallization. The optical isomers can be resolved using any of the conventional optical resolution techniques to give optically pure isomers. Such a resolution can be performed in any chiral synthetic intermediate as well as in the products of general formula I. The optically pure isomers can also be individually obtained using enantiospecific synthesis. The present invention covers the individual isomers as well as their mixtures (e.g. racemic mixtures), whether as obtained by synthesis or by physically mixing them up.

The invention also provides processes for preparing the compounds of formula I. The precise method used for the preparation of a given compound of the present invention may vary depending on its chemical structure. Scheme 1 illustrates the general method for their preparation.

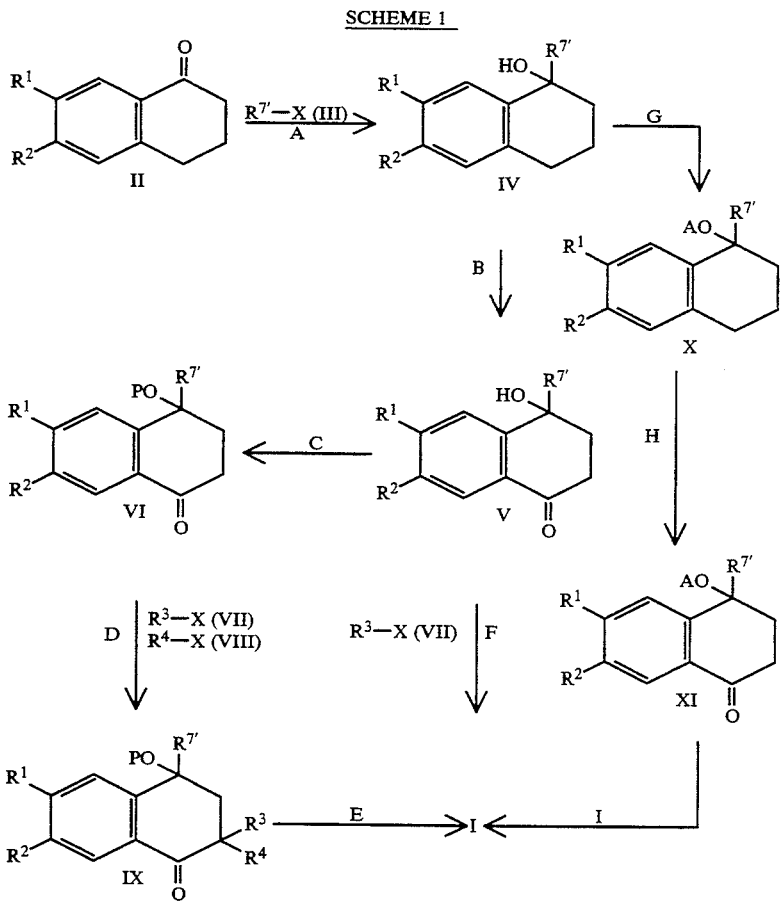

SCHEME 1

Wherein:

R$^1$, R$^2$, R$^3$ and R$^4$ have the previously defined meaning;

A represents a C$_{1-4}$ alkyl group;

R$^{7'}$ represents a 2-, 3- or 4-pyridyl group which can be optionally substituted by a hydroxy group;

X means chlorine, bromine or iodine;

P means a hydroxy protecting group such as a trialkylsilyl group.

The preparation of the compounds of general formula I starts from the tetralones of general formula II, which either are known compounds (see, for example, R. W. Griffin, J. D. Gass, M. A. Berwick, R. S. Shulman, *J. Org. Chem.*, 1964, 29, 2109) or else, if they have not been described, can be prepared following analogous methods to those described in the literature.

The reaction of tetralones II (Step A) with a compound of general formula $R^{7'}$—X (III, wherein $R^{7'}$ and X have the previously defined meaning) in the presence of a base such as butyl lithium in a suitable solvent such as diethyl ether, at a temperature between $-50°$ C. and room temperature and during a reaction time from 30 rain to 24 h, leads to the compounds of general formula IV.

In Step B, a compound of formula IV is allowed to react with an oxidant such as potassium permanganate in a suitable solvent such as acetone at a temperature between room temperature and that of the boiling point of the solvent and during a reaction time from 6 to 48 h, to give a compound of formula V.

In Step C, the hydroxy group of a compound of general formula V is protected to give a compound of general formula VI. As protecting group of the hydroxy function can be used any group which is stable to the subsequent reaction conditions, such as a trialkylsilyl group. The introduction of the trialkylsilyl group is performed by reacting the compound of formula V with a trialkylsilyl halide or trialkylsilyl trifluoromethanesulfonate in a suitable solvent such as methylene chloride at a reaction temperature between $0°$ C. and room temperature and during a reaction time from 1 to 24 h.

The reaction of a compound of formula VI (Step D) with an equivalent of a base such as sodium hydride or butyl lithium and an alkylating agent of general formula $R^3$—X (VII, wherein $R^3$ and X have the previously defined meaning) in an inert solvent such as benzene or tetrahydrofuran, at a temperature between $-20°$ C. and that of the boiling point of the solvent and during a period of time from 2 to 48 h, leads to the compounds of general formula IX wherein $R^3$ is $C_{1-4}$ alkyl and $R^4$ is hydrogen. The subsequent alkylation with one more equivalent of base and an alkylating agent of general formula $R^4$—X (VIII, wherein $R^4$ and X have the previously defined meaning) leads to the compounds of general formula IX wherein $R^3$ and $R^4$ are $C_{1-4}$ alkyl groups. When $R^3$ and $R^4$ are the same, dialkylation of VI can be performed directly, by using two equivalents of base and an excess of alkylating agent in the same experimental conditions described above. In case $R^3$ and $R^4$ together form a $C_{2-5}$ polymethylene chain, the compounds of formula IX are obtained by alkylation with 2 equivalents of base and an alkylating agent of formula X—$(CH_2)p$—X, wherein X has the previously defined meaning and p is 2, 3, 4 or 5.

The deprotection of the hydroxy group of the compounds of general formula IX (Step E) leads to the compounds of general formula I wherein $R^5$ is hydrogen, $R^6$ is OH and $R^7$ is a 2-, 3- or 4-pyridyl group which can be optionally substituted by a hydroxy group. The reagent and the reaction conditions needed will depend on the nature of the protecting group used. Thus, if the protecting group is trialkylsilyl, deprotection can be carried out by treatment with tetrabutylammonium fluoride in a suitable solvent such as tetrahydrofuran at a reaction temperature between $-15°$ and $50°$ C. and during a reaction time from 2 to 24 h.

Alternatively, the compounds of general formula I wherein $R^5$ is hydrogen, $R^6$ is OH and $R^3$ and $R^4$ are the same can be obtained directly from the compounds of formula V (Step F) by treatment with three equivalents of base and two equivalents of alkylating agent in the same experimental conditions mentioned above for Step D, thus avoiding the steps of protection and deprotection of the hydroxy group.

The compounds of formula I wherein $R^5$ is hydrogen and $R^6$ is $C_{1-4}$ alkoxy can be obtained from the corresponding hydroxy derivatives (I, wherein $R^5$=H, $R^6$=OH) by treatment with one equivalent of a base such as sodium hydride or butyl lithium and an alkylating agent of formula A-X (wherein X has the previously defined meaning and A is $C_{1-4}$ alkyl) in the same experimental conditions mentioned above for Step D. Alternatively, in case A, $R^3$ and $R^4$ are the same, said compounds can be directly obtained from a compound of formula V by treatment with three equivalents of base and an excess of alkylating agent in the same experimental conditions described above.

Alternatively, the compounds of formula I wherein $R^5$ is hydrogen and $R^6$ is $C_{1-4}$ alkoxy can also be obtained by a sequence which comprises the following steps: reaction of a compound of formula IV (Step G) with an alkylating agent of formula A-X in the same experimental conditions mentioned above for Step D, to give a compound of formula X; reaction of X (Step H) with an oxidant such as potassium permanganate in the same experimental conditions mentioned above for Step B, to give a compound of formula XI; and finally, alkylation of XI (Step I) following the procedure described in Step D.

Compounds of general formula I wherein $R^5$ and $R^6$ together with the ring carbon atom form a double bond can be obtained from the compounds of formula I wherein $R^5$ is hydrogen and $R^6$ is hydroxy or $C_{1-4}$ alkoxy by treatment with p-toluenesulfonic acid in a suitable solvent such as toluene or xylene in a Dean-Stark apparatus at the temperature of the boiling point of the solvent and during a reaction time enough to distill off one equivalent of water.

Optionally, the double bond between positions 3 and 4 in a compound of formula I may be reduced by treatment with hydrogen in the presence of a catalyst such as palladium on charcoal in a polar solvent such as ethanol at a temperature between room temperature and $100°$ C. at a pressure between 1 and 10 atm and during a reaction time from 1 to 48 h, to give a compound of formula I wherein $R^5$ and $R^6$ are hydrogen.

The compounds of formula I wherein $R^7$ represents a 2-, 3- or 4-pyridyl group whose nitrogen atom is in form of the N-oxide can be obtained from the corresponding compounds of formula I wherein $R^7$ is 2-, 3- or 4-pyridyl by treatment with a peracid such as m-chloroperbenzoic acid in a suitable solvent such as methylene chloride at a temperature between $0°$ C. and room temperature and during a reaction time from 6 to 24 h. Optionally, when in the corresponding compound of formula I $R^5$ and $R^6$ form together with the ring carbon a double bond, said bond can be epoxidated simultaneously to the oxidation of the pyridinic nitrogen by treatment with an excess of peracid in the same experimental conditions.

The compounds of general formula I wherein $R^5$=OH and $R^6$=H can be obtained by hydrogenation of a compound of formula I, wherein $R^5$ and $R^6$ form together with the ring carbons an epoxide group, with hydrogen in the presence of a catalyst such as Pd on C in a polar solvent such as ethanol at a temperature between room temperature and $100°$ C. at a pressure between 1 and 10 atm and during a reaction time from 1 to 48 h.

Furthermore, it is also possible to transform the groups $R^1$ and/or $R^2$ in a compound of formula I or in one of its synthetic intermediates into other groups $R^1$ and/or $R^2$.

Thus, for example, a bromine atom can be converted into a cyano group by treatment with an excess of cuprous cyanide (I) in a polar solvent of high boiling point such as N-methylpyrrolidone at a temperature between room temperature and that of the boiling point of the solvent and during a reaction time from 2 to 48 h.

Moreover, a cyano group may be transformed into a carboxyl group (e.g. with HCl in water, 20°–100° C.), into a carbamoyl group (e.g. with KOH in t-BuOH), into a methyl carboximidate group (e.g. with sodium methoxide in MeOH, room temperature), or into a methyl carboxylate group (e.g. with HCl gas in MeOH, reflux); a bromine atom may be converted into a trifluoromethyl or a pentafluoroethyl group (e.g. with trifluoroacetate or pentafluoropropanoate resp./cuprous iodide in NMP, 160° C.), or into a trimethylsilylethynyl group (e.g. with Pd(II) acetate/ethynyltrimethylsilane/triphenylphosphine in NEt$_3$), which may be subsequently transformed into an ethynyl group (e.g. with potassium carbonate in MeOH, room temperature); a methoxy group may be transformed into a hydroxy group (e.g. with 48% HBr, reflux), and this one may be then converted into a bromine atom (e.g. with trimethylphosphonium bromide, 185° C.).

The compounds of formula I may be transformed into their corresponding acid addition salts following standard procedures, for example by treatment with an acid, such as hydrochloric acid, sulphuric acid, nitric acid, oxalic acid or methanesulfonic acid.

The compounds of general formula I are useful as antihypertensive agents, as shown by their ability to inhibit the noradrenaline induced contractions in isolated rat portal vein, according to test 1, and their ability to lower the blood pressure in hypertensive rats, according to test 2.

Test 1: Inhibition of noradrenaline induced contractions in isolated rat portal vein.

Portal vein was extracted from adult male rats (b.w. 200–250 g), that had been stunned and exanguinated. Vein strips were suspended in an isolated organ bath (Letica) containing a physiological saline solution continuously bubbled with 5% $CO_2$, 95% $O_2$ gas at 37° C., pH 7.2. Contractions were induced by noradrenaline (3 $\mu$M) and were reverted after thorough washing with physiological saline solution. Portal vein contraction was measured with an isometric force transducer at an initial tension of 1 g. After two equal contractions with noradrenaline, performed in order to measure the tissue's basal response, the test compounds were incubated for 30 minutes and a new contraction was induced. The concentration that produces a 50% inhibition (IC$_{50}$) versus the basal response was calculated. The experiment was repeated at least two times and the mean was calculated. The results are shown in table I.

TABLE I

| Compound N° | IC$_{50}$ ($\mu$M) |
|---|---|
| 4 | 0.8 |
| 10 | 0.9 |
| 12 | 0.2 |

TABLE I-continued

| Compound N° | IC$_{50}$ ($\mu$M) |
|---|---|
| 15 | 0.6 |
| 18 | 0.5 |

Test 2: Lowering of the arterial pressure in conscious spontaneously hypertensive rats.

Spontaneously hypertensive male rats (b.w. 200–250 g) were used. Diastolic and systolic arterial pressure were measured at the caudal artery using a sphygnomanometer (Letica 5007 and 5007/4) attached to the animal's tail. To ensure rapid and reliable data, animals were placed on a heating plate at 37° C., with the aim of producing a vasodilatation that ensured better fixation of the rat tail to the transducer chamber. During the experiment, rats were conscious and fixed by a clamp. The test products were administered orally. Arterial pressure was measured every 60 minutes over a period of 4 hours and 10 minutes before the administration of the test compound. The drop in the arterial pressure was calculated for each compound at a dose of 0.1 mg/Kg, using at least 4 animals. The results are shown in table II.

TABLE II

| Compound N° | Pressure Drop (mm Hg) ± SEM (0.1 mg/Kg p.o.) |
|---|---|
| 4 | 53 ± 8 |
| 10 | 53 ± 15 |
| 12 | 95 ± 9* |
| 15 | 98 ± 20 |
| 18 | 74 ± 42 |

(*)Compound 12 was administered at a dose of 1 mg/Kg p.o.

Furthermore, we have found that compounds of general formula I are bronchodilator agents, according to test 3.

Test 3 -Direct relaxation of isolated guinea pig tracheal spirals.

Tracheae were extracted from male guinea pigs of (b.w. 400 g) that had been stunned and exanguinated. Then, tracheae were cut in zigzag sections and placed in an isolated organ bath (Letica) containing Krebs-Henseleit solution at 37° C., pH 7.4, continuously bubbled with carbogen (95% $O_2$ and 5% $CO_2$). The relaxation of the tracheae was measured using an isometric force transducer. The basal tension was 0.5 g. The test compounds were cumulatively added to the bath and the effective concentration that produced 50% of the maximum relaxation (EC$_{50}$) was calculated. The maximum relaxation was taken to be the relaxation induced by isoproterenol at $1 \times 10^{-6}$M. The experiment was repeated at least two times and the mean was calculated. Results are shown in table III.

TABLE III

| Compound N° | EC$_{50}$ ($\mu$M) |
|---|---|
| 4 | 0.2 |
| 10 | 0.2 |
| 12 | 3.0 |
| 15 | 0.1 |
| 18 | 0.2 |

Solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides that could exhibit controlled liberation. Soft gelatin capsules are possible wherein the active ingredient is mixed with water or an oily medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, methylcellulose, hydroxypropylmethylcellulose, sodium alginate, polyvinylpyrrolidone, gum tragacanth, xantham gum, gum acacia, and one or more preservatives, such as methyl or n-propyl-p-hydroxybenzoate. Additional excipients, for example sweetening, flavouring and colouring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavouring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also be administered in the form of suppositories for rectal administration of the drug, or as creams, ointments jellies, solutions or suspensions for topical use and pessaries for vaginal administration.

The dosage and frequency of dose may vary depending upon symptoms, age and body weight of the patient, as well as upon the route of administration, but, in general, the compounds of the invention may be administered orally in a daily dose of from 0.1–100 mg for an adult, preferably a dosage from 2–50 rag, which may be administered either as a single dose or as divided doses. A preferred dosage for human patients is from 0.001 to 5 mg/Kg of body weight, more preferably from 0.01 to 1 mg/Kg of body weight.

Following are some representative preparations for tablets, capsules, syrups, aerosols and injectables. They can be prepared following standard procedures and they are useful in the treatment of diseases related with the regulation of the smooth muscle contraction, in the cardiovascular and respiratory systems and in the gastrointestinal, urinary and uterus tracts, and particularly as antihypertensive and bronchodilator agents.

| Tablets | |
|---|---|
| Compound of formula I | 70 mg |
| Dibasic calcium phosphate | 125 mg |
| Sodium starch glycolate | 10 mg |
| Talc | 42.5 mg |
| Magnesium stearate | 2.5 mg |
| | 250.0 mg |
| Hard gelatin capsules | |
| Compound of formula I | 70 mg |
| Lactose | 227 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 g |
| Water to | 100 mL |
| Aerosol | |
| Compound of formula I | 4 g |
| Flavouring agent | 0.2 g |
| Propylene glycol to | 100 mL |
| Suitable propellent to | 1 unit |
| Injectable preparation | |
| Compound of formula I | 70 mg |
| Benzylic alcohol | 0.05 mL |
| Propylene glycol | 1 mL |
| Water to | 5 mL |

The following examples illustrate, but do not limit, the scope of the preparation of the compounds of the present invention.

REFERENCE EXAMPLE 1

(+)-7-Bromo-1-hydroxy-1-(2-pyridyl)-1,2,3,4-tetrahydronaphthalene

To a solution of 54.2 mL (0.088 mol) of n-BuLi 1.6 m in hexane was added at −45° C. a solution of 7.20 mL (0.076 mol) of 2-bromopyridine in 33 mL of anhydrous ether and the mixture was stirred under an argon atmosphere for 10 min. 16.44 g (0.073 mol) of 7-bromo-1,2,3,4-tetrahydronaphthalen-1-one (R. W. Griffin, J. D. Gass, M. A. Berwick, R. S. Shulman, J. Org. Chem., 1964, 29, 2109) in 100 mL of anhydrous ether was added and the mixture was stirred at −30° C. for 2 h. The mixture was then allowed to warm up to room temperature. 50 mL of 1N HCl was added and the layers were separated. The organic phase was extracted with 1N HCl and the combined aqueous phases were basified with 1N NaOH. The precipitate thus obtained was filtered and dried, to afford 15.27 g of a white solid (yield: 69%). A sample was purified by chromatography on silica gel ($CH_2Cl_2$-hexane) to give the analytically pure product.

M.p.: 119°–120° C.;

IR (KBr) v: 3500–3100, 2938, 1583, 1467, 1427, 1405, 1177, 1020, 786 $cm^{-1}$;

$^1$-RMN (80MHz, $CDCl_3$)δ(TMS): 8.57 (d,J=5Hz,1H,pyr), 7.61(t of d,J=8Hz, J=1.6Hz, 1H, Ar), 7.4–6.9 (m, 5H, Ar), 5.85 (s, 1H, OH), 2.9 (m, 2H, $CH_2Ar$), 2.0 (m, 4H, $2CH_2$);

Analysis Calcd. for $C_{15}H_{14}BrNO$: C 59.23%; H 4.64%; N 4.60%. Found: C 59.23%: H 4.70%; N 4.54%.

REFERENCE EXAMPLE 2

(+)-6-Bromo-4-hydroxy-4-(2-pyridyl)-1,2,3,4-tetrahydronaphthalen-1-one

To a solution of 16.27 g (0.053 mol) of the product obtained in reference example 1 in 1.5 L of acetone, was added 40.3 g (0.25 mol) of $KMnO_4$ in 36 mL of $H_2O$ and the mixture was stirred at reflux overnight. The resulting suspension was filtered and the solvent was removed. The residue was dissolved in $H_2O$ and extracted with $CH_2Cl_2$. The organic phase was dried over $MgSO_4$ and the solvent was removed, to afford a residue that was chromatographed on silica gel (hexane-ethyl acetate). The title compound of this example was obtained as a white solid (3.40 g, yield: 20%) together with 6.01 g of the starting product (yield: 37%). By repeating this operation 1.45 g more of product was obtained (yield: 9%).

M.p.: 125.9°–126.5° C.;

IR (KBr) v: 3500–3100, 2963, 2929, 1659, 1579, 1453, 1436, 1426, 1414, 1365, 1336, 1314, 1282, 1252, 1176, 1162, 1097, 1088 $cm^{-1}$;

$^1$H-RMN (80MHz,$CDCl_3$)δ(TMS): 8.66(d,J=5Hz,1H,pyr),7.97(d,J=8Hz,1H, Ar),7.6(m,2-H,Ar),7.3(m,2H,Ar),6.93(d,J=8Hz,1H,Ar),5.83(s,1-H,OH), 3.2–2.3(m,4H,$2CH_2$);

Analysis Calcd. for $C_{15}H_{12}BrNO_2$: C 56.63%; H 3.80%, N 4.40%. Found: C 56.58%; H 3.78%; N 4.33%.

REFERENCE EXAMPLE 3

(±)-6-Bromo-4-(2-pyridyl)-4-trimethylsilyloxy-1,2,3,4-tetrahydronaphthalen-1-one To a solution of 0.5 g (1.57 mmol) of the product obtained in reference example 2 and 0.22 mL (1.57 mmol) of triethylamine in 9.5 mL of anhydrous $CH_2Cl_2$ was added at 0° C. under an argon atmosphere 0.33 mL (1.71 mmol) of trimethylsilyl trifluoromethanesulfonate and the resulting mixture was stirred at 0 ° C. for 1 h. The mixture was poured into cold water and extracted with diethyl ether. The organic phase was dried over $MgSO_4$ and the solvent was removed, to afford a residue that was chromatographed on silica gel (hexane-ethyl acetate). The title compound of the example was obtained as a yellow semisolid (0.17 g, yield: 28%) together with 0.10 g of the starting material (yield: 20%).

IR (KBr) v: 3058, 2953, 1676, 1579, 1456, 1278, 1249, 1140, 1110, 1074, 840, 748 $cm^{-1}$;

$^1$H-RMN (80MHz, $CDCl_3$)δ8.45 (broad d, J=4.8Hz, 1H, pir),7.89(dd, J=7.4Hz, J=1.5Hz,1H,Ar),7-.7–7.0(m,5H,Ar),3.0–2.3(m,4H,$2CH_2$),0.0(s,9H,3Me).

(±)-6-Bromo-2,2-dimethyl-4-(2-pyridyl)-4-trimethylsilyloxy-1,2,3,4-tetrahydronaphthalen-1-one To a solution of 0.17 g (0.44 mmol) of the product obtained in reference example 3 and 0.11 mL (1.74 mmol) of IMe in 3 mL of anhydrous tetrahydrofuran was added, at −20° C. under an argon atmosphere, 46 mg (1.06 mmol) of 55% sodium hydride previously washed with hexane. The resulting mixture was stirred for 2 h at −10 ° C. and then for 3 h at room temperature. Some drops of water were added and the solvent was removed. The residue was redissolved in ethyl acetate and washed with water. The organic phase was dried over $MgSO_4$ and the solvent was removed, to afford a residue that was chromatographed on silica gel (hexane-ethyl acetate), to give the title compound of the example as an oil (0.080 g, yield: 44%).

IR (KBr) v: 3057, 2951, 1676, 1580, 1427, 1249, 1208, 1105, 1063, 898, 839, 752 $cm^{-1}$;

$^1$H-RMN (80MHz, $CDCl_3$)δ8.52(broad d, J=5Hz, 1H, pir), 7.99 (d, J=8.3Hz, 1H, Ar), 7.8–7.1 (m, 5H, Ar), 2.82 (d, J=13.9Hz, 1H, 1H, $CH_2$), 2.31 (d,J=13.9Hz, 1H,$CH_2$), 1.43 (s, 3H, Me), 1.02 (s, 3H, Me), 0.0(s, 9H, 3Me).

REFERENCE EXAMPLE 5

(±)-7-Bromo-1-methoxy-1-(2-pyridyl)-1,2,3,4-tetrahydronaphthalene

Following the procedure described in reference example 4, but using 1 equivalent of NaH and 2 equivalents of methyl iodide and starting from the compound obtained in reference example 1, the title compound of this example was obtained as a white solid (yield: 100%).

M.p.: 104° C.;

IR (KBr) v: 2943, 2923, 1575, 1476, 1456, 1425, 1182, 1160, 1098, 1079, 1053 $cm^{-1}$;

$^1$H-RMN (80MHz, $CDCl_3$)δ8.55 (broad d, J=5Hz, 1H, pyr), 7.7–6.9 (m, 6H, Ar), 3.22 (s, 3H, OMe), 2.81 (t,J=6.4Hz, 2H, $CH_2$), 2.30 (m, 2H, $CH_2$), 1.90 (m, 2H,$CH_2$).

REFERENCE EXAMPLE 6

(+)-6-Bromo-4-methoxy-4-(2-pyridyl)-1,2,3,4-tetrahydronaphthalen-1-one

Following the procedure described in reference example 2, but starting from the compound obtained in reference example 5, the title compound of this example was obtained as a white solid (yield: 48%).

M.p.: 135° C.;

IR (KBr) v: 2930, 2909, 1679, 1577, 1275, 1183, 1102, 1074, 828, 751 $cm^{-1}$;

$^1$H-RMN (80MHz, $CDCl_3$)δ: 8.60 (broad d, J=5Hz, 1H, pyr), 7.97 (d,J=8Hz, 1H, Ar), 7.8–7.1 (m, 5H, Ar), 3.28 (s, 3H, OMe), 3.0–2.5 (m, 4H, $2CH_2$).

REFERENCE EXAMPLE 7

(+)-7-pentafluoroethyl-1,2,3,4-tetrahydronaphthalen-1-one (+)-7-Pentafluoroethyl-1,2,3,4-tetrahydronaphthalen-1-one To a solution of 10 g (0.044 mol) of 7-bromo-1,2,3,4-tetrahydronaphthalenone in 300 mL of N-methylpyrrolidone was added 32.23 g (0.17 mol) of CuI and 31.59 g (0.17 mol) of sodium pentafluoropropanoate and the mixture was heated for 3 h at reflux under an argon atmosphere. After cooling to room temperature, the resulting suspension was poured into a mixture of H₂O—Et₂O (1:1) and filtered over celite. The layers were separated and the organic phase was washed with H₂O and dried over MgSO₄. The solvent was removed, to afford a residue that was chromatographed on silica gel (hexane-AcOEt), to give the desired product as a colourless oil (8.75 g, yield: 80%).

IR (KBr) v: 3034, 2921, 1848, 1686, 1612, 1330, 1298, 1251, 1205, 1151, 1128, 1093, 992 cm⁻¹;

¹H-RMN (80MHz, CDCl₃)δ: 8.29 (s, 1H, Ar), 7.68 (d,J=8Hz, 1H, Ar), 7.40 (d, J=8Hz, 1H, Ar), 3.04 (t,J=5.6Hz, 2H, CH₂),2.72 (t,J=4.8Hz, 2H, CH₂), 2.21(m,2H,CH₂).

REFERENCE EXAMPLE 8

(±)-1-Hydroxy-7-pentafluoroethyl-1-(2-pyridyl)-1,2,3,4-tetrahydronaphthalene

Following the procedure described in reference example 1, but starting from the compound obtained in reference example 7, the title compound of this example was obtained as a colourless oil (yield: 63%).

IR (KBr) v: 3600–3200, 2935, 1587, 1428, 1329, 1293, 1203, 1090 cm⁻¹;

¹H-RMN (80MHz,CDCl₃)δ: 8.58(d,J=4Hz,1H,Ar),7.7–7.0(m,5-H,Ar),6.87(d,J=8Hz,1H,Ar),5.89(broad s.,1H,OH),2.57(m,2H,CH₂),2.3–1.7(m,4H,2CH₂).

REFERENCE EXAMPLE 9

(+)-4-Hydroxy-6-pentafluoroethyl-4-(2-pyridyl)-1,2,3,4-tetrahydronaphthalen-1-one Following the procedure described in reference example 2, but starting from the compound obtained in reference example 8, the title compound of this example was obtained as a white solid (yield: 21%).

M.p.: 91°-93 ° C.;

IR (KBr) v: 3600–3200, 2959, 1692, 1290, 1211, 1175, 1143, 1134, 1098 cm⁻¹;

¹H-RMN (80MHz, CDCl₃)δ: 8.67(d,J=4.8Hz, 1H, Ar), 8.22 (d,J=8Hz, 1H, Ar), 7.8–7.2 (m,4H,Ar), 6.90 (d,J=8Hz, 1H,Ar), 5.86 (broad s. 1H, OH), 3.3–2.4(m, 4H,2CH₂).

REFERENCE EXAMPLE 10

(±)-6,7-Dichlor-1-hydroxy-1-(2-pyridyl)-1,2,3,4-tetrahydronaphthalene

Following the procedure described in reference example 1, but starting from 6,7-dichloro-1,2,3,4-tetrahydronaphthalen-1-one, the title compound of this example was obtained as a white solid (yield: 65%).

M.p.: 69°-71 ° C.;

IR (KBr) v: 3600–3200, 2932, 1462, 1427, 1204, 1191, 1025, 884, 749 cm⁻¹;

¹H-RMN(80MHz,CDCl₃)δ:
8.57(d,J=4Hz,1H,Pyr),7.63(td,J=8Hz,J=1.6Hz,1H-,Pyr),7.4–7.0(m,4H,Ar),5.87(broad s.,1H,OH),2.86(m,2H,CH₂),2.3–1.8(m,4H,2CH₂).

REFERENCE EXAMPLE 11

(+)-6,7-Dichloro-4-hydroxy-4-(2-pyridyl)-1,2,3,4-tetrahydronaphthalen-1-one

Following the procedure described in reference example 2, but starting from the compound obtained in reference example 10, the title compound of this example was obtained as a colourless oil (yield: 15%).

IR (KBr) v: 3600–3200, 2932, 1462, 1427, 1204, 1191, 1025, 884, 749 cm⁻¹;

¹H-RMN(80MHz,CDCl₃)δ:
8.65(d,J=4.8Hz,1H,Pir),8.15(s,1-H,Ar),7.69(td,J=8Hz,J=1.6Hz,1H,Pir),7.32(m,2-H,Ar),6.97(d,J=8Hz,1H,Ar),5.83(broad s.,1H,OH),3-.2–2.4(m,4H,2CH₂).

EXAMPLE 1

(+)-6-Bromo-2,2-dimethyl-4-hydroxy-4-(2-pyridyl)-1,2,3,4-tetrahydronaphthalen-1-one To a solution of 2 g (0.006 mol) of the product obtained in reference example 2 and 0.84 mL (0.013 mol) of MeI in 60 mL of anhydrous tetrahydrofuran was added, at 0° C. under an argon atmosphere, 0.98 g (0.02 mol) of 55% sodium hydride previously washed with hexane and the resulting mixture was stirred at room temperature overnight. Some drops of methanol were added and the solvent was removed. The residue was redissolved in ethyl acetate and washed with H₂O. The organic phase was dried over MgSO₄ and the solvent was removed, to afford a residue that was chromatographed on silica gel (hexane-ethyl acetate). The title compound of this example was obtained together with (±)-6-bromo-2,2-dimethyl-4-methoxy-4-(2-pyridyl)-1,2,3,4-tetrahydronaphthalen-1-one in a ratio 80:20 (1.94 g, yield: 72%), which can be directly used in the next step. A sample was recrystallized from CHCl13-hexane, to give an analytically pure white solid.

Alternatively, the title compound of this example can be obtained by treatment of the product obtained in reference example 4 with tetrabutylammonium fluoride in tetrahydrofuran (yield: 80%).

M.p.: 98.6°–100.7° C.;

IR (KBr) v: 3600–3200, 2984, 2954, 1670, 1578, 1374, 1202, 1141 cm⁻¹;

¹H-RMN(80MHz,CDCl₃)δ(TMS):
8.61(d,J=5Hz,1H,pyr),7.93(d,J=8Hz,1H, Ar), 7.8–6.8 (m, 5H, Ar),6.14 (s, 1H, OH), 2.50 (d,J=14Hz, 1H, CH₂), 2.18, 14Hz, 1H, CH₂), 1.45 (s, 3H, Me), 1.17 (s, 3H, Me);

¹³C-RMN(20MHz,CDCl₃)δ(TMS):
26.03(q),27.44(q),42.03(s),51.08(t),72.77(s), 121.51 (d), 122.89 (d), 128.93 (s), 129.21 (d), 130.26 (s), 131.99 (2d), 137.49 (d), 147.24 (d), 147.50 (s), 163.85 (s), 202.41 (s).

Analysis Calcd. for C₁₇H₁₆BrNO₂·0.1Hexane: C 59.56%; H 4.91%, N 3.95%. Found: C 59.78%; H 4.74%; N 4.18%.

EXAMPLE 2

(+)-6-Bromo-2,2-dimethyl-4-methoxy-4-(2-pyridyl)-1,2,3,4-tetrahydronaphthalen-1-one Following the procedure described in example 1, but using 3.3 equivalents of NaH and 6 equivalents of methyl iodide, the title compound of this example was obtained as a colourless oil (yield: 75%).

The title compound of this example can also be obtained following the procedure described in example 1, but starting from the product described in reference example 6 (yield: 85%).

IR (KBr) v: 2921, 1677, 1580, 1459, 1427, 1220, 1207, 1062 cm⁻¹;

¹H-RMN(80MHz,CDCl₃)δ(TMS):
8.58(m,1H,Ar),7.99(d,J=8Hz,1H,Ar),7.8–7.1(m,5-H,Ar),3.17(s,3H,CH₃),2.71(d,J=14Hz,1H,CH₂),2.32(d-,J=14Hz,1H,CH₂),1.43(s,3H,Me),1.27(s,3H,Me);

MS (GC, CI, Isobutane): 360–362;

13C-RMN(20MHz,CDCl3)δ(TMS):
27.61(q),28.19(q),41.48(s),47.70(t),52.22(q), 80.69 (s), 120.35 (d), 122.19 (d), 127.75 (s), 130.10 (d), 131.60 (s), 132.01 (d), 132.78 (d), 136.75 (d), 143.75 (s), 149.28 (d), 162.34 (s), 202.36 (s).

EXAMPLE 3

6-Bromo-1,2-dihydro-2,2-dimethyl-4-(2-pyridyl)naphthalen-1-one

To a solution of 0.5 g (1.44 mmol) of the product obtained in example 1 in 40 mL of toluene was added a tip of spatula of p-toluenesulfonic acid and the mixture was stirred at reflux with a Dean-Stark apparatus for 5 days. The solvent was removed and the residue was redissolved in ethyl acetate and washed with H2O. The aqueous phase was basified and extracted again with ethyl acetate- The combined organic phases were dried over MgSO4 and the solvent was removed, to afford a residue that was chromatographed on silica gel (hexane-ethyl acetate). The title compound of this example was obtained as a white solid (0.28 g, yield: 60%).

The title compound of this example can also be obtained following the procedure described, but starting from the compound prepared in example 2 and using xylene as solvent (yield: 58%).

M.p.: 66.2°–68.6° C.;

IR (KBr) v: 2962, 2921, 1659, 1572, 1461, 1425, 1346, 1265, 1230, 1078 cm$^{-1}$;

1H-RMN(80MHz,CDCl3)δ(TMS):
8.71(d,J=5Hz,1H,pyr),8.0–7.2(m,6H,Ar), 6.28 (s, 1H, CH=), 1.38 (s, 6H, 2Me);

Analysis Calcd. for C17H14BrNO·0.1Hexane: C 62.74%; H 4.57%, N 4.16%. Found: C 63.08%; H 4.25%; N 4.32%.

EXAMPLE 4

6-Bromo-1,2-dihydro-2,2-dimethyl-4-(N-oxide-2-pyridyl)naphthalen-1-one

To a solution of 0.10 g (0.3 mmol) of the product obtained in example 3 in 3 mL of CH2Cl2 was added 0.097 g (0.3 mmol) of m-chloroperbenzoic acid and the mixture was stirred at room temperature for 18 h. The mixture was poured into 20 mL of CH2Cl2 and the resulting solution was washed with H2O and saturated solution of NaHCO3. The organic phase was dried over MgSO4 and the solvent was removed, to yield a residue that was chromatographed on silica gel (hexane-ethyl acetate). The title compound of this example was obtained as a white solid (0.036 g, yield: 35%).

M.p.: 165°–168° C.;

IR (KBr) v: 3095, 3068, 2959, 1671, 1578, 1416, 1256, 1242 cm$^{-1}$;

1H-RMN(80MHz,CDCl3)δ(TMS):
8.34(m,1H,pyr),7.98(d,J=8Hz,1H,Ar), 7.6–7.1 (m, 4H, Ar), 6.93 (d,J=1.6Hz, 1H, Ar), 6.26 (s, 1H, CH=), 1.62 (s, 3H,Me), 1.40(s,3H,Me);

Analysis Calcd. for C17H14BrNO2: C 59.32%; H 4.10%, N 4.07%. Found: C 59.21%; H 4.15%; N 4.01%.

EXAMPLE 5

(±)-6-Bromo-2,2-dimethyl-3,4-epoxy-4-(N-oxide-2-pyridyl)-1,2,3,4-tetrahydronaphthalen-1-one To a solution of 0.14 g (0.43 mmol) of the product obtained in example 3 in 10 mL of CH2Cl2 was added 0.267 g (0.85 mmol) of m-chloroperbenzoic acid and the mixture was stirred at room temperature for 18 h. The mixture was poured into 20 mL of CH2Cl2 and the solution was washed with H2O and saturated solution of NaHCO3. The organic phase was dried over MgSO4 and the solvent was removed, to afford a residue that was chromatographed on silica gel (hexane-ethyl acetate). The title compound of this example was obtained as a white solid (0.130 g, yield: 84%).

M.p.: 114°–115° C.;

IR (KBr) v: 2955, 2923, 1667, 1582, 1423, 1253 cm$^{-1}$;

1H-RMN(80MHz,CDCl3)δ(TMS):
8.30(m,1H,pyr),7.92(d,J=8H,1H,Ar), 7.7–7.2 (m, 4H, Ar), 7.02 (d,J=1.6Hz, 1H, Ar), 3.55 (s, 1H, CH), 1.54 (s, 6H,2CH3);

Analysis Calcd. for C17H14BrNO3: C 56.69%; H 3.92%, N 3.89%. Found: C 56.91%; H 4.06%; N 3.75%.

EXAMPLE 6

(±)-6-Bromo-2,2-dimethyl-4-methoxy-4-(N-oxide-2-pyridyl)-1,2,3,4tetrahydronaphthalen-1-one Following the procedure described in example 4, but starting from the product obtained in example 2, the title compound of this example was obtained as a white solid (yield: 56%).

M.p.: 158.4°–160.7° C.;

IR (KBr) v: 2951, 2912, 1674, 1579, 1465, 1417, 1247, 1220, 1194, 1099, 1054, 839, 773 cm$^{-1}$;

1H-RMN(80MHz,CDCl3)δ(TMS):
8.15(m,1H,Ar),7.99(d,J=8.4Hz, 1H,Ar), 7.9–7.2 (m,4H, Ar), 6.95 (d,J=1.7Hz, 1H, Ar), 3.09 (s,3H, CH3), 2.70 (d,J=14.3Hz, 1 H, CH2), 2.52 (d,J=14.3Hz, 1 H, CH2), 1.41 (s,3H, Me), 1.26 (s,3H, Me);

Analysis Calcd. for C18H18BrNO3·0.25H2O: C 56.77%; H 4.86%; N 3.68%. Found: C 57.00%; H 4.85%; N 3.63%.

EXAMPLE 7

(±)-2,2-Dimethyl-4-hydroxy-1-oxo-4-(2-pyridyl)-1,2,3,4-tetrahydronaphthalen-6-carbonitrile To a solution of 0.82 g (2.4 mmol) of the product obtained in example 1 in 7 mL of N-methylpyrrolidone was added 0.308 g (3.4 mmol) of cuprous cyanide (I) and the mixture was stirred at reflux under an argon atmosphere for 4 h. The resulting solution was poured into a 10% ethylendiamine solution and extracted with diethyl ether. The organic phase was washed with H2O and dried over MgSO4. The solvent was removed, to afford a residue that was chromatographed on silica gel (hexane-ethyl acetate) to give 0.46 g of the title compound of this example as a colourless oil (yield: 67%).

1H-RMN(80MHz,CDCl3)δ(TMS):
8.64(d,J=48Hz,1H,pyr),8.14(d,J=8Hz, 1H, Ar),7.65 (m,2H, Ar), 7.4–7.2 (m, 2H, Ar), 6.91 (d,J=8Hz, 1H, Ar), 6.27(s,1H,OH), 2.54 (d,J=14.6Hz, 1H, CH2), 2.21 (d,J=14.6Hz, 1H, CH2), 1.47 (s, 3H, ME), 1.22 (s, 3H, Me).

EXAMPLE 8

(+)-2,2-Dimethyl-4-hydroxy-4-(N-oxide-2-pyridyl)-1-oxo-1,2,3,4-tetrahydronaphthalen-6-carbonitrile Following the procedure described in example 4, but starting from the compound obtained in example 7, the title compound of this example was obtained as a white solid (yield: 60%).

M.p.: 219°–220° C.;

IR (KBr) v: 3400–2700, 2227, 1685, 1426, 1404, 1300, 1228, 1192, 983, 836 cm$^{-1}$;

¹H-RMN(80MHz,CDCl₃)δ(TMS): 8.4–7.9(m,3-H,Ar),7.8(dd,J=8Hz,J=1.6Hz, 1H,Ar), 7.2 (m,2H,Ar), 6.45 (dd,J=7.4Hz, J=2.4Hz, 1H, Ar), 3.26 (d, J=14Hz, H,CH₂),2.51(d,J=14Hz, 1H, CH₂),1.58 (s,1H,OH),1.28(s,3H,Me), 0.85(s,3H,Me);

Analysis Calcd. for C₁₈H₁₆N₂O₃: C 70.12%; H 5.23%, N 9.09%. Found: C 69.89%; H 5.60%; N 8.71%.

EXAMPLE 9

1,2-Dihydro-2,2-dimethyl-4-(2-pyridyl)-1-oxonaphthalen-6-carbonitrile

Following the procedure described in example 7, but starting from the compound obtained in example 3, the title compound of this example was obtained as a white solid (yield: 60%).

M.p.: 89° C.;
IR (KBr) ν: 2962, 2923, 2227, 1669, 1582, 1461, 1426, 1346, 1265, 1228 cm⁻¹;
¹H-RMN(80MHz,CDCl₃)δ(TMS): 8.51(d,J=5Hz,1H,pyr),8.0–7.2(m,6H,Ar), 6.25(s,1H,CH=), 1.39 (s,6H,2Me);

EXAMPLE 10

1,2-Dihydro-2,2-dimethyl-4-(N-oxide-2-pyridyl)-1-oxonaphthalen-6-carbonitrile

Following the procedure described in example 3, but starting from the compound obtained in example 8, the title compound of this example was obtained as a white solid (yield: 30%).

M.p.: 166.5°–167.8° C.;
IR (KBr) ν: 2967, 2229, 1671, 1417, 1402, 1246, 1222, 850, 759 cm⁻¹;
¹H-RMN (80MHz, CDCl₃)δ(TMS): 8.4–8.1 (m,2H, Ar), 7.6–7.0 (m, 5H, Ar), 6.33(s, 1H, CH=), 1.42(s,6H, 2Me);

Analysis Calcd. for C₁₈H₁₄N₂O₂·0.25H₂O: C 73.24%; H 4.92%, N 9.51%. Found: C 73.37%; H 4.76%; N 9.43%.

EXAMPLE 11

(±)-2,2-Dimethyl-4-(2-pyridyl)-1-oxo-1,2,3,4-tetrahydronaphthalen-6-carbonitrile To a solution of 0.13 g (0.47 mmol) of the product obtained in example 9 in 3 mL of ethanol was added 0.014 g of 10% Pd/C and the mixture was hydrogenated at atmospheric pressure for 18 h. The catalyst was filtered off and the solvent was removed. The residue was chromatographed on silica gel (hexane-AcOEt) to give the desired product as a colourless oil (0.050 g, yield: 38%).

IR (KBr) ν: 3060, 2921, 2862, 2227, 1679, 1583, 1564, 1468, 1428, 1398, 1301, 1217 cm⁻¹;
¹H-RMN (80MHz, CDCl₃)δ(TMS): 8.62(d,J=4.8Hz, 1H, Ar),8.20 (d,J=8Hz, 1H,Ar), 7.9–7.5(m,2H, Ar), 7.4–7.1 (m,3H, Ar),4.53(Part X of an ABX system, J_AX=11.6Hz, J_BX=5Hz, 1H, CH),2.36 (Part AB of an ABX system, δ_A=2.54, δ_B=2.34, J_AB=13.8Hz,2H,CH₂),1.30(s,6H,2Me).

EXAMPLE 12

(±)-2,2-Dimethyl-4-(N-oxide-2-pyridyl)-1-oxo-1,2,3,4-tetrahydronaphthalen-6-carbonitrile Following the procedure described in example 4, but starting from the compound obtained in example 11, the title compound of this example was obtained as a white solid (yield: 50%).

M.p.: 150°–153° C.;
IR (KBr) ν: 2959, 2918, 1683, 1427, 1398, 1250, 1218, 1170 cm⁻¹;
¹H-RMN (80MHz,CDCl₃)δ(TMS): 8.27(m,2H,Ar),7.64(d,J=8Hz,1H,Ar), 7.26(m,4H, Ar),6.28(m,1H, CH),2.25(m,2H, CH₂), 1.32 (s,6H, 2CH₃);

Analysis Calcd. for C₁₈H₁₆N₂O₂·0.2H₂O: C 73.13%; H 5.55%, N 9.47%. Found: C 73.53%; H 5.74%; N 8.86%.

EXAMPLE 13

(±)-2,2-Dimethyl-4-methoxy-6-pentafluoroethyl-4-(2-pyridyl)-1,2,3,4-tetrahydronaphthalen-1-one Following the procedure described in example 1, but starting from the compound obtained in reference example 9 and using 3.3 equivalents of NaH and 6 equivalents of methyl iodide, the title compound of this example was obtained as a colourless oil (yield: 47%).

IR (KBr) ν: 2934, 1683, 1582, 1459, 1427, 1331, 1311, 1289, 1204, 1144, 1093, 998 cm⁻¹;
¹H-RMN(80MHz,CDCl₃)δ(TMS): 8.56(d,J=4.8Hz,1H,Ar),8.25(d,J=8Hz,1H, Ar),7.9–7.1 (m,5H,Ar), 3.14 (s, 3H, OMe),2.54(AB system, δ_A=2.69,δ_B=2.39, J_AB=14Hz,2H,CH₂),1.44(s,3H,Me),1.09(s,3H,Me).

EXAMPLE 14

1,2-Dihydro-2,2-dimethyl-6-pentafluoroethyl-4-(2-pyridyl)naphthalen-1-one

Following the procedure described in example 3, but starting from the compound obtained in example 13, the title compound of this example was obtained as a colourless oil (yield: 56%).

IR (KBr) ν: 2951, 1920, 2849, 1679, 1581, 1461, 1330, 1284, 1206, 1141, 1084, 1007 cm⁻¹;
¹H-RMN(80MHz,CDCl₃)δ(TMS): 8.73(d,J=4.8Hz,1H,Ar),8.24(d,J=8Hz,1H, Ar),7.9–7.1 (m,5H, Ar),6.36 (s,1H, CH), 1.42(s,3H, Me),1.28(s, 3H, Me).

EXAMPLE 15

1,2-Dihydro-2,2-dimethyl-4-(N-oxide-2-pyridyl)-6-pentafluoroethylnaphthalen-1-one Following the procedure described in example 4, but starting from the compound obtained in example 14, the title compound of this example was obtained as a white solid (yield: 27%).

M.p.: 161°–163° C.;
IR (KBr) ν: 2934, 1683, 1582, 1459, 1427, 1331, 1311, 1289, 1204, 1144, 1093, 998 cm⁻¹;
¹H-RMN(80MHz,CDCl₃)δ(TMS): 8.3(m,2H,Ar),8.60(d,J=8Hz,1H,Ar),7.34(m,3H, Ar),7.01(s,1H, Ar),6.32 (s,1H, CH),1.42(s,6H, 2Me);

Analysis Calcd. for C₁₉H₁₄F₅NO₂: C 59.54%; H 3.68%, N 3.65%. Found: C 59.26%; H 3.71%; N 3.73%.

EXAMPLE 16

(±)-6,7-Dichloro-2,2-dimethyl-4-methoxy-4-(2-pyridyl)-1,2,3,4-tetrahydronaphthalen-1-one Following the procedure described in example 1, but starting from the compound obtained in reference example 11 and using 3.3 equivalents of NaH and 6 equivalents of methyl iodide, the title compound of this example was obtained as a colourless oil (yield: 50%).

IR (KBr) v: 2925, 2823, 1683, 1581, 1454, 1427, 1381, 1306, 1213, 1105, 1063 cm$^{-1}$;

$^1$H-RMN(80MHz,CDCl$_3$)δ(TMS): 8.58(s,1H,Ar),8.2–6.9(m,5H,Ar),3.17(s, 3H,OMe),2.54 (AB system, δ$_A$=2.69,δ$_B$=2.36, J$_{AB}$=14Hz,2H,CH$_2$),1.42(s,3H,Me),1.07(s,3H, Me).

EXAMPLE 17

6,7-Dichloro-1,2-dihydro-2,2-dimethyl-4-(2-pyridyl)-naphthalen-1-one

Following the procedure described in example 3, but starting from the compound obtained in example 16, the title compound of this example was obtained as a colourless oil (yield: 60%).

M.p.: 79°–82° C.;

IR (KBr) v: 2917, 2848, 1666, 1580, 1460, 1427, 1342, 1216 cm$^{-1}$;

$^1$H-RMN(80MHz,CDCl$_3$)δ(TMS): 8.58(d,J=4Hz,1H,Ar),8.2–7.2(m,5H,Ar), 6.30(s,1H,CH),1.39(s,3H, Me),1.26(s,3H, Me).

EXAMPLE 18

6,7-Dihydro-1,2-dihydro-2,2-dimethyl-4-(N-oxide-2-pyridyl)naphthalen-1-one

Following the procedure described in example 4, but starting from the compound obtained in example 17, the title compound of this example was obtained as a white solid (yield: 43%).

M.p.: 187°–193° C.;

IR (KBr) v: 2965, 1670, 1579, 1416, 1249, 759 cm$^{-1}$;

$^1$H-RMN(80MHz,CDCl$_3$)δ(TMS): 8.36 (m,1H,Ar),8.17(s,1H,Ar),7.38(m, 3H,Ar),7.26(s,1H, Ar),6.89(s,1H, Ar),6.26 (s,1H,CH),1.40(s,6H, 2Me);

Analysis Calcd. for C$_{17}$H$_{14}$Cl$_2$NO$_2$·0.25H$_2$O: C 60.44%; H 4.00%, N 4.15%. Found: C 60.22%; H 4.07%; N 4.10%.

We claim:

1. A compound of formula I:

[Structure of formula I with substituents R$^1$, R$^2$, R$^3$, R$^4$, R$^5$, R$^6$, R$^7$ on a naphthalen-1-one core]

wherein:

R$^1$ and R$^2$ independently represent hydrogen, C$_{1-4}$ alkyl, hydroxy, C$_{1-4}$ alkoxy, formyl, C$_{1-4}$ alkylcarbonyl, C$_{1-4}$ alkylthiocarbonyl, carboxyl, C$_{1-4}$ alkoxycarbonyl, C$_{1-4}$ alkoxythiocarbonyl, C$_{1-4}$ alkylcarbonyloxy, C$_{1-4}$ alkylthiocarbonyloxy, hydroxy-(C$_{1-4}$) alkyl, mercapto-(C$_{1-4}$) alkyl, perfluoro-(C$_{1-4}$) alkyl, nitro, amino, cyano, halogen, trifluoromethoxy, ethynyl, trimethylsilylethynyl, C$_{1-4}$ alkylsulfinyl, arylsulfinyl, C$_{1-4}$ alkylsulfonyl, arylsulfonyl, C$_{1-4}$ alkoxysulfinyl, C$_{1-4}$ alkoxysulfonyl, C$_{1-4}$ alkylcarbonylamino, C$_{1-4}$ alkoxycarbonylamino, aminosulfinyl, aminosulfonyl, aminocarbonyl, aminothiocarbonyl, C$_{1-4}$ alkylsulfinylamino, C$_{1-4}$ alkylsulfonylamino, C$_{1-4}$ alkoxysulfinylamino, C$_{1-4}$ alkoxysulfonylamino, (C$_{1-4}$ alkyl)carbonyl(C$_{1-4}$ alkyl), nitro-(C$_{1-4}$ alkyl), cyano-(C$_{1-4}$ alkyl), (C$_{1-4}$ alkyl)C(=NOH), (C$_{1-4}$ alkyl)C(=NNH$_2$) or (C$_{1-4}$ alkoxy)C(=NH), the above amino groups being optionally substituted by one or two C$_{1-4}$ alkyl groups;

R$^3$ and R$^4$ are the same or different and independently represent a C$_{1-4}$ alkyl group, or R$^3$ and R$^4$ together form a C$_{2-5}$ polymethylene chain;

R$^5$ is hydrogen and then R$^6$ represents hydrogen, hydroxy or C$_{1-4}$ alkoxy, or R$^5$ is hydroxy and then R$^6$ is hydrogen, or else R$^5$ and R$^6$ together with the ring carbons form a bond or a group of formula:

[epoxide structure: C—C with O bridge]

R$^7$ is a 2-, 3- or 4-pyridyl radical which can be optionally substituted by a hydroxy group or whose nitrogen atom can be optionally in the form of the N-oxide; or pharmaceutically acceptable salt or solvate thereof.

2. A compound according to claim 1 wherein R$^1$, R$^2$, R$^5$, R$^6$ and R$^7$ have the previously defined meaning; and
R$^3$ and R$^4$ are methyl.

3. A compound according to claim 1 wherein R$^5$, R$^6$ and R$^7$ have the previously defined meaning; R$^3$ and R$^4$ are methyl;
R$^1$ represents halogen, cyano, C$_{1-4}$ alkyl, C$_{1-4}$ alkylsulfonyl, arylsulfonyl, perfluoro(C$_{1-4}$)alkyl or ethynyl; and
R$^2$ represents hydrogen or R$^1$.

4. A compound according to claim 1 wherein R$^5$ and R$^6$ have the previously defined meaning;
R$^3$ and R$^4$ are methyl;
R$^1$ represents halogen, cyano, C$_{1-4}$ alkyl, C$_{1-4}$ alkylsulfonyl, arylsulfonyl, perfluoro(C$_{1-4}$)alkyl or ethynyl;
R$^2$ represents hydrogen or R$^1$; and
R$^7$ represents a 2-(N-oxide)pyridyl group.

5. 6-Bromo-1,2-dihydro-2,2-dimethyl-4-(N-oxide-2-pyridyl)naphthalen-1-one or a salt or solvate thereof.

6. 1,2-Dihydro-2,2-dimethyl-4-(N-oxide-2-pyridyl)-1-oxonaphthalen-6-carbonitrile or a salt or solvate thereof.

7. (±)-2,2-Dimethyl-4-(N-oxide-2-pyridyl)-1-oxo-1,2,3,4-tetrahydronaphthalen-6-carbonitrile or a salt or solvate thereof.

8. 1,2-Dihydro-2,2-dimethyl-4-(N-oxide-2-pyridyl)-6-pentafluoroethylnaphthalen-1-one or a salt or solvate thereof.

9. 6,7-Dichloro-1,2-dihydro-2,2-dimethyl-4-(N-oxide-2-pyridyl)naphthalen-1-one or a salt or solvate thereof.

10. A pharmaceutical composition which comprises an effective amount of a compound of formula I as defined in claim 1 or a pharmaceutically acceptable salt thereof or a pharmaceutically acceptable solvate thereof in admixture with a pharmaceutically acceptable excipient.

11. A method or treating hypertension or asthma of a warm-blooded animal, comprising administering to an animal in need thereof an effective amount of a compound as claimed in claim 1, or a pharmaceutically-acceptable salt or solvate thereof.

12. A method for the treatment or prevention of asthma in a warm-blooded animal, comprising administering to an animal in need thereof an effective amount of a compound as claimed in claim 1, or a pharmaceutically-acceptable salt or solvate thereof.

13. A method according to claim 12 wherein the effective amount is from about 0.001 to 5 mg/Kg of body weight.

14. A method according to claim 13 wherein the effective amount is from about 0.001 to 1 mg/Kg of body weight.

15. A method for the treatment or prevention of hypertension in a warm-blooded animal, comprising administering to an animal in need thereof an effective amount of a compound as claimed in claim 1, or a pharmaceutically-acceptable salt or solvate thereof.

16. A method according to claim 15 wherein the effective amount is from about 0.001 to 5 mg/Kg of body weight.

17. A method according to claim 15 wherein the effective amount is from about 0.01 to 1 mg/Kg of body weight.

18. A method according to claim 11 wherein said compound is 6-bromo-1,2-dihydro-2,2-dimethyl-4-(N-oxide-2-pyridyl)naphthalen-1-one.

19. A method according to claim 11 wherein said compound is 1,2-dihydro-2,2-dimethyl-4-(N-oxide-2-pyridyl)-1-oxonaphthalen-6-carbonitrile.

20. A method according to claim 11 wherein said compound is (±)-2,2-dimethyl-4-(N-oxide-2-pyridyl)-1-oxo-1,2,3,4-tetrahydronaphthalen-6-carbonitrile.

21. A method according to claim 11 wherein said compound is 1,2-dihydro-2,2-dimethyl-4-(N-oxide-2-pyridyl)-6-pentafluoroethylnaphthalen-1-one.

22. A method according to claim 11 wherein said compound is 6,7-dichloro-1,2-dihydro-2,2-dimethyl-4-(N-oxide-2-pyridyl)naphthalen-1-one.

23. A method according to claim 11 wherein the compound is administered orally and the effective amount is from 0.001 to 5 mg/Kg of body weight.

24. A method according to claim 23 wherein the effective amount is from 0.01 to 1 mg/Kg of body weight.

* * * * *

UNITED STATES PATENT AND TRADEMARK OFFICE
CERTIFICATE OF CORRECTION

PATENT NO. : 5,356,915                    Page 1 of 2
DATED : October 18, 1994
INVENTOR(S) : C. Almansa et al.

It is certified that error appears in the above-indentified patent and that said Letters Patent is hereby corrected as shown below:

Column 3, line 65, "R4-X" should be -- $R^4$-X --; Col. 4, line 61, "$C^{1-4}$" should be -- $C_{1-4}$ --; Col. 5, line 27, "tert-butoxy" should be -- tertbutoxy --; Col. 8, line 43, "alkylsulfinylamino" should be -- alkylsulfinylamino --; Col. 9, line 28, "C1-4" should be -- $C_{1-4}$ --; Col. 9, line 31, "2cyanoethyl" should be -- 2-cyanoethyl --; Col. 12, structure 15, "$Q^-$" should be -- $O^-$ --; Col. 15, line 6, "I I" should be -- II --; Col. 15, line 12, "rain" should be -- min --; Col. 15, line 49, "$R^4$together" should be -- $R^4$ together --; Col. 16, line 64, "$R^6$form" should be -- $R^6$ form --; Col. 20, line 9, "rag" should be -- mg --; Col. 20, line 55, "(+)" should be -- (±) --; Col. 21, line 10, "$^1$-RMN" should be -- $^1$H-RMN --; Col. 21, line 14 should be moved up to line 13 because it is the continuation of line 13; Col. 21, line 19, "(+)" should be -- (±) --; Col. 22, line 1, insert the subheading -- REFERENCE EXAMPLE 4 --; Col. 22, line 20, after "$CDCl_3$)" insert space; before "8.52" insert a colon and space; after "8.52" insert space; Col. 22, line 39, after "$CDCl_3$)" insert space; before "8.55" insert a colon and space; Col. 22, line 45, "(+)" should be -- (±) --; Col. 22, lines 59-60 should be deleted; Col. 22, line 62, "(+)" should be -- (±) --; Col. 23, line 32, "(+)" should be -- (±) --; Col. 23, line 63, "(+)" should be -- (±) --; Col. 24, line 10, "(+)" should be -- (±) --; Col. 24, line 41, after "2.18," insert -- (d, J= --; Col. 24, line 52, "(+)" should be -- (±) --; Col. 26, line 18, "4tetrahydronaphthalen" should be -- 4-tetrahydronaphthalen --; Col. 26, line 52, "48 Hz" should be -- 4.8 Hz --;

UNITED STATES PATENT AND TRADEMARK OFFICE
CERTIFICATE OF CORRECTION

PATENT NO. : 5,356,915
DATED : October 18, 1994
INVENTOR(S) : C. Almansa et al.

It is certified that error appears in the above-indentified patent and that said Letters Patent is hereby corrected as shown below:

Col. 26, line 56, "ME)" should be -- Me) --; Col. 26, line 60, "(+)" should be -- (±) --; Col. 27, line 4, before "H, CH$_2$)" insert -- 1 --; Col. 29, line 24, "6,7-Dihydro" should be -- 6,7-Dichloro --; <u>In the Claims:</u> Col. 30, line 56, claim 11, "method or" should be -- method for --; Col. 31, line 2, claim 14, "0.001" should be -- 0.01 --.

Signed and Sealed this

Twenty-first Day of February, 1995

Attest:

BRUCE LEHMAN

Attesting Officer

Commissioner of Patents and Trademarks